(12) United States Patent
Eyer et al.

(10) Patent No.: US 7,608,420 B2
(45) Date of Patent: Oct. 27, 2009

(54) PROCESS FOR THE RECOVERY OF STAUROSPORINE FROM A FERMENTATION BROTH

(75) Inventors: Kurt Eyer, Visp (CH); Georges Kalbermatten, Ausserberg (CH); Jean-Peal Roduit, Sion (CH); Alain Wellig, Schweiz (CH)

(73) Assignee: Lonza AG, Basel (CH)

( * ) Notice: Subject to any disclaimer, the term of this patent is extended or adjusted under 35 U.S.C. 154(b) by 325 days.

(21) Appl. No.: 10/553,911

(22) PCT Filed: Apr. 19, 2004

(86) PCT No.: PCT/EP2004/004127

§ 371 (c)(1),
(2), (4) Date: Oct. 21, 2005

(87) PCT Pub. No.: WO2004/094645

PCT Pub. Date: Nov. 4, 2004

(65) Prior Publication Data

US 2006/0194294 A1 Aug. 31, 2006

(30) Foreign Application Priority Data

Apr. 22, 2003 (EP) ................... 03009172

(51) Int. Cl.
*C12P 1/00* (2006.01)
(52) U.S. Cl. ........................ 435/41; 540/545
(58) Field of Classification Search ........... None
See application file for complete search history.

(56) References Cited

U.S. PATENT DOCUMENTS

| 4,107,297 | A |   | 8/1978  | Omura et al.       |         |
|-----------|---|---|---------|--------------------|---------|
| 4,567,143 | A |   | 1/1986  | Matson             |         |
| 4,637,981 | A | * | 1/1987  | Hershberger et al. | 435/75  |
| 4,935,415 | A |   | 6/1990  | Nakano et al.      |         |
| 4,973,552 | A |   | 11/1990 | Schroeder et al.   |         |
| 5,015,578 | A |   | 5/1991  | Schroeder et al.   |         |
| 5,073,633 | A |   | 12/1991 | Schroeder et al.   |         |
| 5,135,857 | A | * | 8/1992  | Borghi et al.      | 435/71.3 |
| 5,344,926 | A |   | 9/1994  | Murakata et al.    |         |

FOREIGN PATENT DOCUMENTS

| EP | 0238011 | 9/1987 |
| EP | 0388962 | 9/1990 |
| EP | 0444503 | 9/1991 |
| EP | 0579955 | 1/1994 |

OTHER PUBLICATIONS

Nabais et al. "Ultrafiltration of fermemnted broths and solvent extraction of antibiotics" Bioprocess Engineering (1995) 13: 215-221.*
Morioka et al., Agric. Biol. Chem., (1985), 49 (7) 1959-1963.
Oka et al., Agric. Biol. Chem., (1986), 50, 2723-2727.
Takahashi et al., Actinomycetologica, (1995), 19-26.

* cited by examiner

*Primary Examiner*—Sandra Saucier
*Assistant Examiner*—Susan Hanley
(74) *Attorney, Agent, or Firm*—Fisher, Christen & Sabol

(57) ABSTRACT

Staurosporine of the formula (I) is recovered from a fermentation broth in a process comprising an ultrafiltration and a diafiltration step.

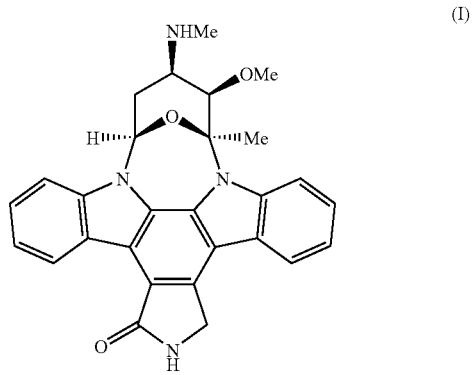

16 Claims, No Drawings

PROCESS FOR THE RECOVERY OF STAUROSPORINE FROM A FERMENTATION BROTH

This application is a 371 U.S. national application of International Patent Application PCT/EP2004/004127, filed on Apr. 19, 2004, that has priority benefit of European Patent Application 03009172.2, filed on Apr. 22, 2003.

The present invention refers to a process for the recovery of staurosporine from a fermentation broth.

Staurosporine is known to have antimicrobial activity against yeasts and fungi as well as hypotensive activity in mammals (U.S. Pat. No. 4,107,297). In addition, staurosporine serves as the starting material for the preparation of (7R)-(+)-7-hydroxystaurosporine, which has anti-tumor activity and antibacterial activity (EP 0 238 011 B1, EP 0 575 955 A1).

The production of staurosporine by fermentation of microorganisms of the family Actinomycetes is known in the art and various processes for the recovery of staurosporine from the respective fermentation broths have been described.

U.S. Pat. No. 4,107,297 describes the recovery of staurosporine (designated as AM-2282) from a fermentation broth of a microorganism of the genus *Streptomyces*. The fermentation broth was extracted with butyl acetate and the butyl acetate layer was transferred into aqueous HCl. The pH of the aqueous layer was adjusted to 10, and the aqueous layer was extracted with ethyl acetate. Silica gel chromatography followed by recrystallization yielded staurosporine.

Morioka et al. *Agric. Biol. Chem.* 1985, 49(7), 1959-1963 describes the recovery of staurosporine (designated as NB-2025) from a fermentation broth of a microorganism of the genus *Streptomyces*. The fermentation broth was filtered and the wet cell cake was extracted with methanol. The methanol extract was combined with the filtrate and concentrated in vacuo. The concentrate was extracted with ethyl acetate. Two silica gel chromatographies and two recrystallizations afforded staurosporine.

Oka et al. *Agric. Biol Chem.* 1986, 50, 2723-2727 also describes the recovery of staurosporine from a fermentation broth of a microorganism of the genus *Streptomyces*. The fermentation broth was centrifuged and Amberlite XAD-2 was added to the supernatant. The resin was first washed and then staurosporine was eluted. The eluate was concentrated in vacuo and extracted with butanol. Amberlite CG-50 ($H^{30}$) chromatography was performed and the fractions containing staurosporine were treated with Amberlite IR 45 ($OH^-$). Silica gel chromatography followed by recrystallization yielded staurosporine.

EP 0 444 503 A2 again describes the recovery of staurosporine from a fermentation broth of a microorganism of the genus *Streptomyces*. The fermentation broth was filtered and the wet cell cake was stirred in tetrahydrofuran, filtered and washed with acetone. The filtrate was concentrated until the aqueous layer remained, brine was added and the aqueous layer was extracted with chloroform. Silica gel chromatography followed by two Sephadex LH-20 chromatographies afforded staurosporine.

The main drawbacks of the above processes for the recovery of staurosporine from a fermentation broth are the extraction steps using a water-immiscible organic solvent and the chromatographic purification steps. Staurosporine is only poorly soluble in water-immiscible organic solvents such as butanol, ethyl acetate, butyl acetate, chloroform and methylene chloride. Therefore an efficient extraction of staurosporine requires large volumina of water-immiscible organic solvents. Chromatographic purification steps are time-consuming and use large volumes of eluents.

It is an object of the present invention to provide an economic process for the recovery of staurosporine from a fermentation broth.

This object is achieved by the process according to the invention.

The process of the present invention for the recovery of staurosporine of the formula

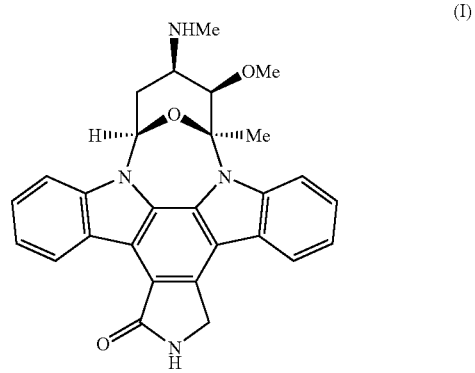

from a fermentation broth comprises the steps of
i) adding a water-miscible organic solvent A to the fermentation broth,
ii) ultrafiltrating the dilute fermentation broth obtained in step i),
iii) diafiltrating the retentate obtained in step ii) with a mixture of water and a water-miscible organic solvent B,
iv) optionally adjusting the pH of the permeates obtained in steps ii) and iii) to at least 8.5,
v) concentrating the permeates obtained in steps ii) and iii) until the water-miscible organic solvents A and B are almost completely removed,
vi) adjusting the pH of the concentrate obtained in step v) to at least 8.5, unless the pH of said concentrate is already at least 8.5 and
vii) collecting the precipitated staurosporine (I) obtained in step vi).

The process of the present invention can be employed for the-recovery of staurosporine from the fermentation broth of any microorganism which is capable of producing staurosporine. Microorganisms of the family Actinomycetes are known to be capable of producing staurosporine. Examples of microorganisms of the family Actinomycetes are microorganisms of the genera *Actinomadura*, *Nocardia*, *Streptomyces* or *Saccharothrix*. An example of a microorganism of the genus *Streptomyces* is *Streptomyces hygroscopicus* C39280-450-9 (ATCC 53730; EP 0 444 503 A2). An example of a microorganism of the genus *Saccharothrix* is *Saccharothrix aerocolonigenes* subsp. *staurosporea* R10069 (ATCC 55006), formerly known as *Streptomyces* sp. AM-2282 (FERM-P No. 3722, NRRL 11,184; U.S. Pat. No. 4,107,297; Takahashi et al. *Actinomycetologica* 1995,9, 19-26).

The fermentation of microorganisms capable of producing staurosporine is known in the art. The microorganism can be fermented in liquid medium after inoculation with a suitable inoculum under any conditions suitable for that particular microorganism, either in batch, fed-batch or continuous mode. Microorganisms of the genus *Streptomyces* can be fermented under aerobic conditions, at a pH between 6.0 and 8.0 and at a temperature between 24 to 36° C. When such microorganism of the genus *Streptomyces* is fermented in a batch-mode, mono-, di- or polysaccharides or mixtures thereof can be used as the main source of carbon and energy at an initial concentration of at least 5% (w/v). Examples of suitable monosaccharides are glucose, mannose, galactose and fructose. Examples of suitable disaccharides are maltose, cellobiose, lactose and sucrose. Examples of polysaccharides are starch and cellulose. Batch mode operation includes fed-batch mode operation in the present context; preferably, it is a simple batch mode fermentation in its strict sense.

The process of the present invention for the recovery of staurosporine from a fermentation broth can also be adapted to the recovery of the mirror image or enantiomer of staurosporine from a fermentation broth. The enantiomeric or mirror image of staurosporine can be recovered from the fermentation broth of any microorganism which is capable of producing it.

The fermentation broth obtained directly from the fermentation can be optionally diluted with water before the addition of water-miscible organic solvent A. Therefore, in the present context fermentation broth refers either to the fermentation broth that as directly obtained from the fermentation or to the fermentation broth which is diluted with water after the fermentation. Preferably, the concentration of mono-, di- or polysaccharide in the fermentation broth is less than 5% (w/v) before the addition of water-miscible organic solvent A. Preferably, the cells of the fermentation broth are not disrupted before the addition of water-miscible organic solvent A.

The water-miscible organic solvents A and B may be identical or different and may be any water-miscible organic solvent which dissolves staurosporine (I) and which can be almost completely removed from water by distillation. Preferably, the water-miscible organic solvents A and B are identical or different and are selected from the group consisting of $C_{1-3}$-alcohols, tert-butanol, acetone and tetrahydrofuran. $C_{1-3}$-alcohols are methanol, ethanol, propanol and 2-propanol. More preferably, the water-miscible organic solvents A and B are identical or different and are selected from the group consisting of methanol, acetone and tetrahydrofuran. Most preferably, the water-miscible organic solvents are identical and are tetrahydrofuran.

Preferably, the ratio of fermentation broth/water-miscible organic solvent A is between 5:1 and 0.5:1 (w/w). More preferably, it is between 3:1 and 1.5:1 (w/w). Most preferably, it is between 2.5:1 and 1.9:1 (w/w).

Preferably, the mixture of fermentation broth and water-miscible organic solvent A is agitated for at least 0.5 h before the ultrafiltration, more preferably, for at least 1 h.

The ultrafiltration can be performed using a ceramic, polymeric or metallic membrane under pressure. Preferably, the ultrafiltration is performed using a membrane having a molecular weight cut-off of 20 kDa or less, more preferably of 10 kDa or less, at a temperature of in between 10 and 50° C, more preferably of in between 15 and 40° C. More preferably, the membrane used is a ceramic membrane. Most preferably, the membrane used is a Unipektin ceramic membrane of the type UF 50 3X. The ultrafiltration may be conducted in a dead-end or tangential flow filtration mode.

Preferably, the ratio of permeate/retentate after the ultrafiltration is between 5:1 and 0.25:1 (w/w). More preferably, it is between 3:1 and 0.5:1 (w/w). Most preferably, it is between 1.8:1 and 1.2:1 (w/w).

The diafiltration can be performed in a continuous or discontinuous mode. In the continuous mode, essentially an ultrafiltration as specified above is carried out concomitant with diluting the retenate. Such continuous-mode diafiltration is preferably carried out in a tangential flow mode. A discontinuous diafiltration comprises the steps of first diluting the retenate and secondly ultrafiltrating the diluted retenate essentially as described above. Such discontinuous diafiltration may comprise several cycles of dilution and filtration. Preferably according to the present invention, the diafiltration is performed in a discontinuous mode consisting of at least 2 cycles. Preferably, the ratio of retentate/mixture of water and water-miscible organic solvent B is between 5:1 and 0.5:1 (w/w). More preferably, it is between 3:1 and 1:1 (w/w).

Preferably, the ratio of water/water-miscible organic solvent B of the mixture of water and water-miscible organic solvent B is between 5:1 and 0.5:1 (w/w). More preferably, it is between 3:1 and 1.5:1 (w/w). Most preferably, it is between 2.5:1 and 1.9:1 (w/w).

Preferably, the retentate and the mixture of water and water-miscible organic solvent B are agitated for at least 5 min before the diafiltration, more preferably for at least 15 min. Preferably, the diafiltration is performed at a temperature of between 10 and 50° C., more preferably of between 15 and 40° C.

The permeate of the ultrafiltration and the permeate of the diafiltration can be combined before the concentration step. Preferably, the pH of the permeates is adjusted to at least 8.5, more preferably to at least 10.0, before the concentration step.

Preferably, the permeates are concentrated by distillation under vacuo at a pressure of below 600 mbar, more preferably, of below 400 mbar.

Almost complete removal of the water-miscible organic solvents A and B means that content of water-miscible organic solvents A and B in the concentrate is less than 10% (w/w), preferably less than 5% (w/w), more preferably less than 2.5% (w/w), most preferably less than 1%.

If the water-miscible organic solvents A or/and B form an azeotrope with water, appropriate distillation techniques can be applied.

During the distillation staurosporine may already precipitate.

After the distillation, the pH of the concentrate is adjusted to at least 8.5, unless the pH of the concentrate is already at least 8.5. Preferably the pH of the concentrate is adjusted to at least 10.0, more preferably to at least 12.0, most preferably to at least 13.0. The precipitated staurosporine is now collected, for example by centrifugation or filtration. Preferably, it is collected by centrifugation. More preferably, it is collected by centrifugation using a Westfalia Separator centrifuge type B7.

Preferably, staurosporine obtained in step vii) is recrystallized from any suitable solvent system. Examples of suitable solvent systems are chloroform, methylene chloride, ethyl acetate, $C_{1-3}$-alcohols, tert-butanol, acetone, 1,4-dioxane, tetrahydrofuran, an acetone/water mixture, a $C_{1-3}$-alcohol/water mixture water, a tetrahydrofuran/water mixture and a tetrahydrofuran/methanol mixture. More preferably, staurosporine is recrystallized from a solvent system consisting of acetone, an acetone/water mixture and a tetrahydrofuran/methanol mixture. Most preferably, staurosporine is recrystallized from a tetrahydrofuran/methanol mixture.

Preferably, the recrystallization includes the filtration of a solution of dissolved staurosporine. More preferably, this filtration is performed in the presence of a filtration aid such as Celite®.

EXAMPLE 1

Production of staurosporine by fermentation of a staurosporine producing microorganism of the genus *Streptomyces*.

1.1. Preparation of a Pre-Pre-Culture

A sterile medium (50 g, pH 7.0) containing 2% (w/v) glucose, 1.5% (w/v) peptone, 0.5% (w/v) corn steep liquor, 0.5% (w/v) NaCl, 0.1% (w/v) $CaCO_3$ and 0.005% (w/v) $FeSO_4 \times 7\ H_2O$ and 0.2% (v/v) Asahi Denka defoaming agent ADEKA NOL LG-109 was inoculated with a suspension of spores of a staurosporine producing microorganism of the genus *Streptomyces* (150 μL). The pre-pre-culture was cultivated at 28° C. and 120 rpm for 72 h.

1.2 Preparation of a Pre-Culture

A sterile medium (1100 g; pH 7.0) containing 2% (w/v) glucose, 1.5% (w/v) peptone, 0.5% (w/v) corn steep liquor, 0.5% (w/v) NaCl, 0.1% (w/v) $CaCO_3$, 0.005% (w/v) $FeSO_4 \times 7\ H_2O$ and 0.2% (v/v) ADEKA NOL LG-109 was inoculated with the pre-pre-culture (ca. 50 mL) obtained in step 1.1. The pre-culture was cultivated at 28° C. and 120 rpm for 24 h.

1.3 Fermentation

A sterile medium (350 kg, pH between 6.8 and 7.2) containing 10% (w/v) sucrose, 4% (w/v) soy bean meal, 0.005% (w/v) $FeSO_4 \times 7\ H_2O$, 0.4% (w/v) $CaCO_3$ and 0.1% (w/v) ADEKA NOL LG-109 was inoculated with the pre-culture (ca. 1.0 L) obtained in step 1.2. The culture was cultivated at 28 to 25° C., 200 to 400 rpm, 50 to 120 kPa and 6 to 20 $Nm^3/h$ (0° C., 101.3 kPa). Production of 392 mg/L staurosporine was reached after 5 days of fermentation.

EXAMPLE 2

Isolation of raw staurosporine from a fermentation broth of a staurosporine producing microorganism of the genus *Streptomyces*

2.1. Ultrafiltration

Water (58 kg) and tetrahydrofuran (183 kg) was added to the fermentation broth (350 kg, 392 mg/L staurosporine content (=134 g staurosporine)) obtained as described in example 1. The diluted fermentation broth was agitated for 1 h, and then concentrated by ultrafiltration over a Unipektin ceramic membrane type UF 50 3X having a molecular weight cut-off of 10 kDa at a temperature from 18 to 35° C. and a pressure of about 2 bar. 351 kg of permeate was obtained.

2.2. Diafiltration

The retentate obtained as described in step 2.1 was diafiltrated four times. Each time water (92 kg) and tetrahydrofuran (42 kg) were added to the retentate, the obtained suspension was agitated for 15 min, and then concentrated by ultrafiltration over the ceramic membrane used in step 2.1 at a temperature of about 32° C. and a pressure of about 2.5 bar. 550 kg of total permeate was obtained.

2.3 Distillation

The permeates obtained as described in steps 2.1 and 2.2 were combined and the pH was adjusted to 10.0 at 20° C. by addition of aqueous NaOH (30% (w/w)). The permeate was concentrated at a temperature of 70° C. and a pressure of 400 mbar until 400 L of total distillate was obtained. During the distillation staurosporine precipitated.

2.4 Centrifugation

After adjusting the pH of the concentrate, which contains precipitated staurosporine, obtained as described in step 2.3 to 13.0 at 20° C. by addition of aqueous NaOH (30% (w/w)), the concentrate was centrifuged in portions using a Westfalia Separator centrifuge type B7 at a speed of 7000 rpm and at a pressure of 2.0 bar. In total 883.4 g wet separator cake (12% (w/w) staurosporine content (=106.0 g staurosporine)) was obtained.

EXAMPLE 3

Recrystallization of Raw Staurosporine

The wet separator cakes obtained as described in example 2 of thirteen fermentation broth obtained as described in example 1 were dissolved in tetrahydrofuran (106 kg). Celite (6.9 kg) was added. The obtained suspension was stirred for 2 h and then filtered. The filter cake was washed with tetrahydrofuran (53 kg). The pH of the combined filtrates was adjusted to 13.5 with aqueous NaOH (2 N), and then the combined filtrates were concentrated to a volume of 65 L at 40° C. and 180 mbar, filtered through a cartridge filter and diluted with methanol (28 kg). After reconcentration to a volume of 40 L, methanol (28 kg) was added again. The solution was reconcentrated to a volume of 28 L, cooled to 3° C. and stirred at that temperature for 1 h. The formed precipitate was collected by filtration, washed with cold (ca. 0° C.) methanol (2.4 kg) and dried at 50 mbar. 1165 g of staurosporine (89% (w/w) stauroporine content (=1037 g staurosporine, 64% recovery yield) was obtained.

The invention claimed is:

1. A process for the recovery of staurosporine of formula:

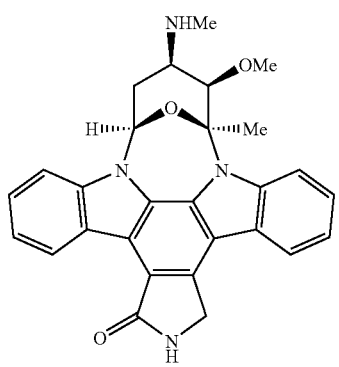

(I)

from a fermentation broth comprising the steps of:
   i) adding tetrahydrofuran to the fermentation broth;
   ii) ultrafiltering the dilute fermentation broth obtained in step i);
   iii) optionally diafiltrating the retenate obtained in step ii) with a mixture of a water and tetrahydrofuran, and optionally combining the permeates of the ultrafiltration and the diafiltration;
   iv) optionally adjusting the pH of the permeate obtained in step ii) or step iii) to at least 8.5;
   v) concentrating the permeate;
   vi) adjusting the pH of the concentrate obtained in step v) to at least pH 8.5, unless the pH of said concentrate is already at least 8.5; and
   vii) collecting the precipitated staurosporine obtained in step vi).

2. The process of claim 1, wherein the ratio of fermentation broth/tetrahydrofuran is between 5:1 and 0.5:1 (w/w).

3. The process of claim 2 wherein the ratio of water/tetrahydrofuran of the mixture of water and tetrahydrofuran is between 5:1 and 0.5:1 (w/w).

4. The process of claim 3 wherein the pH of the permeates obtained in steps ii) and iii) is adjusted to at least 8.5.

5. The process of claim 4 wherein the pH of the concentrate is adjusted to at least 10.0.

6. The process of claim 5 wherein precipitated staurosporine (I) is collected by centrifugation.

7. The process of claim 6 wherein staurosporine (I) obtained in step vii) is recrystallized from a tetrahydrofuran/methanol mixture.

8. The process of claim 1 wherein the ratio of water/tetrahydrofuran the mixture of water and tetrahydrofuran is between 5:1 and 0.5:1 (w/w).

9. The process of claim 1 wherein the pH of the permeates obtained in steps ii) and iii) is adjusted to at least 8.5.

10. The process of claim 1 wherein the pH of the concentrate is adjusted to at least 10.0.

11. The process of claim 1 wherein precipitated staurosporine (I) is collected by centrifugation.

12. The process of claim 1 wherein staurosporine (I) obtained in step vii) is recrystallized from a tetrahydrofuran/methanol mixture.

13. A process for the recovery of staurosporine of formula:

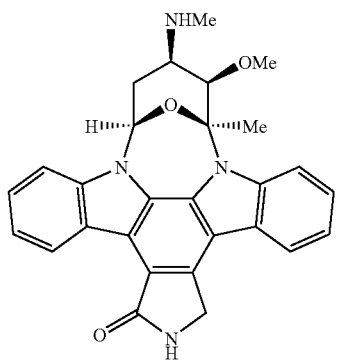

(I)

from a fermentation broth comprising the steps of:
i) adding tetrahydrofuran to the fermentation broth;
ii) ultrafiltering the dilute fermentation broth obtained in step i);
iii) concentrating the permeate obtained in step ii);
iv) adjusting the pH of the concentrate obtained in step iii) to at least pH 8.5, unless the pH of said concentrate is already at least 8.5; and
v) collecting the precipitated staurosporine obtained in step iv).

14. A process for the recovery of staurosporine of formula:

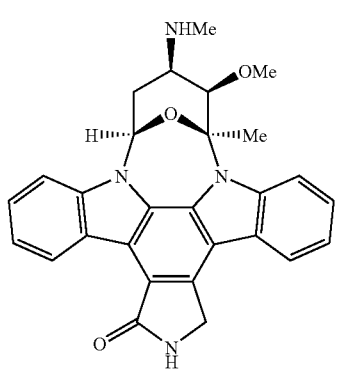

(I)

from a fermentation broth comprising the steps of:
i) adding tetrahydrofuran to the fermentation broth;
ii) ultrafiltering the dilute fermentation broth obtained in step i);
iii) adjusting the pH of the permeate obtained in step ii) to at least 8.5;
iv) concentrating the permeate from step iii);
v) adjusting the pH of the concentrate obtained in step iv) to at least pH 8.5, unless the pH of said concentrate is already at least 8.5; and
vi) collecting the precipitated staurosporine obtained in step v).

15. A process for the recovery of staurosporine of formula:

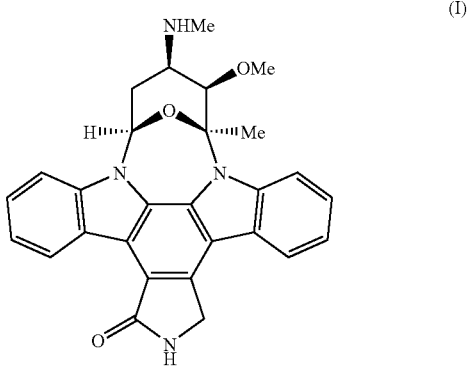

(I)

from a fermentation broth comprising the steps of:
i) adding tetrahydrofuran to the fermentation broth;
ii) ultrafiltering the dilute fermentation broth obtained in step i);
iii) diafiltrating the retenate obtained in step ii) with a mixture of a water and tetrahydrofuran;
iv) adjusting the pH of the permeate obtained in step iii) to at least 8.5;
v) concentrating the permeate from step iv);
vi) adjusting the pH of the concentrate obtained in step v) to at least pH 8.5, unless the pH of said concentrate is already at least 8.5; and
vii) collecting the precipitated staurosporine obtained in step vi).

16. A process for the recovery of staurosporine of formula:

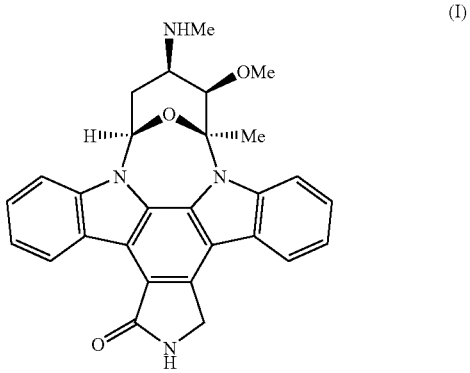

(I)

from a fermentation broth comprising the steps of:
i) adding tetrahydrofuran to the fermentation broth;
ii) ultrafiltering the dilute fermentation broth obtained in step i);

iii) diafiltrating the retenate obtained in step ii) with a mixture of a water and tetrahydrofuran;
iv) combining the permeates of the ultrafiltration and the diafiltration;
v) adjusting the pH of the permeate obtained in step iv) to at least 8.5;
vi) concentrating the permeate from step v);
vii) adjusting the pH of the concentrate obtained in step vi) to at least pH 8.5, unless the pH of said concentrate is already at least 8.5; and
viii) collecting the precipitated staurosporine obtained in step vii).

* * * * *